United States Patent [19]

Thompson et al.

[11] Patent Number: 4,648,261
[45] Date of Patent: Mar. 10, 1987

[54] METHOD FOR DETERMINING PHYSICAL PROPERTIES OF A POROUS SAMPLE USING CAPILLARY PRESSURE MEASUREMENT

[75] Inventors: Arthur H. Thompson, Spring; Alan J. Katz, Houston, both of Tex.

[73] Assignee: Exxon Production Research Co., Houston, Tex.

[21] Appl. No.: 797,107

[22] Filed: Nov. 12, 1985

[51] Int. Cl.$^4$ ............................................. G01N 15/08
[52] U.S. Cl. .......................................................... 73/38
[58] Field of Search ..................................... 73/38, 153

[56] References Cited

U.S. PATENT DOCUMENTS

| | | | |
|---|---|---|---|
| 2,604,779 | 7/1952 | Rurcell | 73/38 |
| 2,641,924 | 6/1953 | Reichertz | 73/38 |
| 2,794,338 | 6/1957 | Murphy et al. | 73/38 |
| 3,438,245 | 4/1969 | Winslow | 73/38 |
| 3,525,251 | 8/1970 | Marcu et al. | 73/38 |
| 3,859,843 | 1/1975 | Lowell | 73/38 |
| 3,882,714 | 5/1975 | Libal et al. | 73/38 |
| 4,211,106 | 7/1980 | Swanson | 73/38 |
| 4,272,983 | 6/1981 | Sisti et al. | 73/38 |

OTHER PUBLICATIONS

M. C. Leverett, "Capillary Behavior in Porous Solids," Trans. AIME, 142, pp. 152–169 (1941).
W. R. Purcell, "Capillary Pressures—Their Measurement Using Mercury and the Calculation of Permeability Therefrom," Pet. Trans. AIME, 186, pp. 39–48 (1949).
B. F. Swanson, "Simple Correlation Between Permeabilitles and Mercury Capillary Pressures, J. Pet. Technol, pp. 2498–2504 (Dec. 1981).
T. Hagiwara, "Archie's m for Permeability", SPE Paper 13100 (1984).

Primary Examiner—Stewart J. Levy
Assistant Examiner—Hezron E. Williams
Attorney, Agent, or Firm—Alfred A. Equitz

[57] ABSTRACT

A method for determining pore-dependent properties, such as electrical conductivity and absolute permeability, of a porous sample by use of capillary pressure measurements. Capillary pressure data are obtained by performing nonwetting fluid intrusion measurements on a sample. The lowest applied pressure at which the intruding fluid forms a connected path spanning the sample (the "threshold capillary pressure") is determined. The sample's conductivity or absolute permeability, or both, may be determined in a preferred embodiment from the characteristic pore diameter corresponding to the threshold capillary pressure, an other parameters extracted from the measured capillary pressure data. The invention does not require use of any arbitrary, empirically adjustable parameter to predict conductivity or permeability. The method may be performed to characterize small samples of porous rock such as those obtained during borehole drilling operations. The invention may also be performed to characterize other types of porous samples, such as porous catalysts or electrode materials used in battery technology.

17 Claims, 8 Drawing Figures

METHOD FOR DETERMINING PHYSICAL PROPERTIES OF A POROUS SAMPLE USING CAPILLARY PRESSURE MEASUREMENT

FIELD OF THE INVENTION

The invention is a method for determining pore-dependent properties, such as electrical conductivity and absolute permeability, of a porous sample by use of capillary pressure measurements. The invention includes the steps of performing nonwetting fluid intrusion measurements on the sample, and determining the pore-dependent properties of interest from the measured capillary pressure data.

BACKGROUND OF THE INVENTION

Many potential uses exist for information relating to the electrical conductivity and the permeability of porous rocks. In petroleum geophysics, the electrical conductivity is related to the oil saturation in a reservoir through the use of the Archie's Law relationship. The permeability is used to estimate the producibility of a reservoir or the facility with which oil may be extracted from a reservoir. The present invention advances the state of the art by providing an accurate method for predicting such pore-dependent properties as electrical conductivity and permeability using nonwetting fluid intrusion measurements.

The methods of the present invention are not restricted to porous rocks, but may find application to many porous materials that have a pore structure with a broad distribution of pore sizes. For example, catalyst support materials are microporous solids containing pores not unlike those in rocks. The methods described herein may be used to predict conductivity and permeability in such porous catalysts. Similarly, the methods may be used to predict the permeability and conductivity of porous electrode materials used in battery technology.

It has long been recognized that there is a relationship between capillary pressure or mercury intrusion curves and permeability. The paper "Capillary Behavior in Porous Solids," by Leverett (M. C. Leverett, *Trans. AIME*, 142, pp. 152-169 (1941)) in the early 1940's laid out one possible relation between capillary pressure and permeability. The pioneering work of this researcher is still in wide-spread use. In 1949, Purcell ("Capillary Pressures-Their Measurement Using Mercury and the Calculation of Permeability Therefrom," W. R. Purcell, *Pet Trans. AIME*, 186, pp. 39-48 (1949)) described a probable relationship between permeability and mercury intrusion and specifically pointed out that if one could make such an association then one could determine permeability from measurements on mud log cuttings. A more recent attempt to predict permeability from capillary pressure curves is disclosed in B. F. Swanson's paper entitled "A Simple Correlation Between Permeabilities and Mercury Capillary Pressures," *J. Pet. Technol.*, pp 2498-2504 (Dec. 1981), which describes a variation on conventional predictions in which the ratio of the pore volume filled by mercury to the pore pressure is maximized. Most recently, T. Hagiwara, in the paper "Archie's m for Permeability," *SPE Paper* 13100 (1984)) extended the B. F. Swanson prediction to include an electrical conductivity measurement in the permeability prediction. Each of these previous attempts to predict permeability or conductivity has been moderately successful. However, each of these methods is semi-empirical, in the sense that the relationship between capillary pressure and permeability or electrical conductivity is basically determined by empirical relationships involving adjustable parameters in the equations relating the various physical parameters.

U.S. Pat. No. 4,211,106, issued July 8, 1980 to B. F. Swanson describes a method and means of predicting permeability from mercury capillary pressure measurements. A nomogram is applied to the capillary pressure data in accordance with the empirical model described in the above cited 1981 paper by Swanson. U.S. Pat. No. 4,211,106 discloses a method based on the empirical nomogram technique. It also describes an apparatus including means for measuring the pressure and volume of mercury inserted into a sample of 1 cc volume or less.

The present invention is very different from the prior art in several essential ways. Most importantly, the method of the present invention is a quantitatively explicit means for determining both the electrical conductivity formation factor and the absolute permeability of a porous medium. The conductivity and permeability are determined with no empirically adjustable parameters. The prior art does not disclose how to determine both conductivity and permeability from a single set of measured capillary pressure data, and the prior art requires use of empirical fitting parameters that could, in general, be different for every porous material.

SUMMARY OF THE INVENTION

The present invention is a method for predicting pore-dependent properties of a porous material from capillary pressure measurements. The invention applies a new model for the absolute permeability and conductivity of rocks. The model connects the permeability to the electrical conductivity and to capillary pressure data resulting from nonwetting fluid intrusion measurements. The predictions of permeability and conductivity obtained give quantitative agreement, within experimental error, between conductivity, permeability and the intruded fluid threshold pressure with no arbitrary adjustable parameters. The invention permits absolute permeability and electrical conductivity to be predicted from measurements on small samples of porous rock such as those obtained during drilling operations.

The first step of the inventive method is to perform a nonwetting fluid intrusion measurement on a porous sample to generate capillary pressure data indicative of the volume of intruded fluid versus applied pressure. The second step is to determine from these data the threshold capillary pressure, $P_c$, and, from the parameter $p_c$, the associated characteristic length, $l_c$, of the sample. The threshold pressure, $p_c$, is the lowest applied pressure at which the intruding fluid forms a connected path spanning the sample.

In one embodiment, several parameters (defined below) are extracted from the capillary pressure data and used with the characteristic length, $l_c$, to determine the sample's permeability and conductivity. In an alternative embodiment wherein the conductivity is known, the permeability is determined from the measured length parameter, $l_c$, and the known conductivity.

The parameter, $p_c$, and the other parameters to be extracted from the capillary pressure data, may be measured from graphs of the capillary pressure data.

DETAILED DESCRIPTION OF THE PREFERRED EMBODIMENTS

Figure 1:
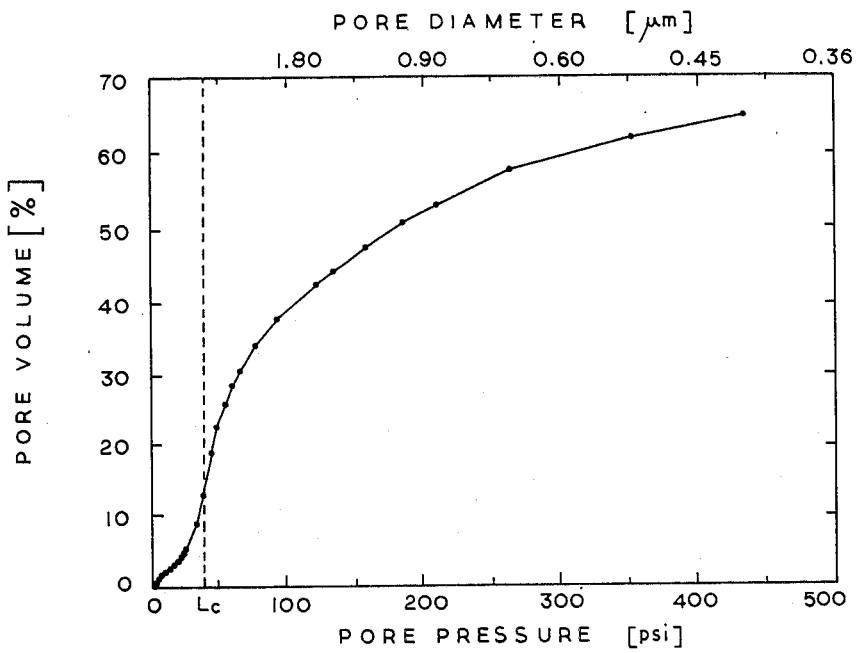
FIG. 1 is a mercury intrusion curve displaying capillary pressure data for a sample consisting of quartz cemented sandstone grains. The vertical scale represents the normalized volume of intruded mercury (i.e. volume of intruded mercury divided by the total pore volume of the sample). The lower horizontal scale represents external pressure applied to the mercury, and the upper horizontal scale represents the local diameter of the pore space associated with each value of applied pressure.

It is important to an understanding of the invention initially to introduce the theoretical model underlying it. The theoretical model is based on percolation concepts. There are two important new components in the model when applied to porous samples such as rocks. The first is that the permeability (and conductivity) are dominated by the fluid flow (charge flow) on the first connected path that is formed when a nonwetting fluid such as mercury is injected into a sample. This path generally includes the largest pore sizes in the rock. The remaining pore volume contains many small pores that are numerous but contribute little to the permeability. The appropriate length scale for the pore diameter is given by the effective capillary diameter, $l_c$, for the first connected mercury path spanning the sample.

A second component of the model is the notion that the connectivity of the pore space is the same for conductivity and permeability.

The implications of the percolation model apply to electrical transport as well as to mass transport, but there are important differences between the two types of transport. The movement of fluid through the pore space (the mass current) is much more sensitively dependent on the local pore width than is the electrical current. This observation reflects the difference, for example, between the hydraulic conductance of a pipe of diameter and length L, which is proportional to a factor of $L^3$, and the electrical conductance of the same pipe filled with an electrolytic solution, which is proportional to a factor of L. Another implication of this difference between the hydraulic and electrical conductances is that the current pathways for the two cases will be weighted differently; that is, certain paths that may contribute insignificantly to the mass current may be of more importance to the electrical current. These differences between the case of mass transport and the case of electrical transport are largely responsible for the differing magnitudes of the constants that appear in Equations (1), (2) and (3) below. The challenge behind understanding mass and ionic transport through the pore space, then, is determining those sets of paths that dominate the two kinds of transport.

We have incorporated the above concepts into the extensive literature on percolation phenomena to yield the following predictions:

$$\sigma/\sigma_o = (l_{max}^\sigma/l_c)\Phi S_{max}^\sigma \quad (1)$$

$$k = (1/84)(l_{max}^k/l_c)(l_{max}^k)^2 \cdot S_{max}^k \Phi; \quad (2)$$

and $$k = (1/217)l_c^2(\sigma/\sigma_o) \quad (3)$$

where k is the absolute permeability, $\Phi$ is the porosity, $l_c$ is the capillary diameter associated with the first connected path, $\sigma$ is the pore-saturated sample conductivity, $\sigma_o$ is the conductivity of the fluid saturating the pore-saturated sample, $l_{max}^\sigma$ is the effective diameter of the path where the product of capillary diameter and the volume of the nonwetting fluid intruded into the sample is a maximum, $S_{max}^\sigma$ is the fraction of connected pore space filled at $l_{max}^\sigma$, $l_{max}^k$ is the effective diameter of the path where the product of the mercury volume and the cube of capillary diameter is a maximum, and $S_{max}^k$ is the fraction of connected pore space filled at $l_{max}^k$. For a single straight pipe the constant in equation (3) would be replaced by c=1/32. In the percolation model, the constant is reduced because the most effective path for fluid flow has an effective pore size that is smaller than $l_c$. In addition, the most effective path for conductivity has a pore size that is slightly smaller than the one for permeability. These refinements lead to a value of 1/217 for c.

Throughout this specification, we shall assume that the porosity, $\Phi$, of the sample in question is known, such as by performing an independent measurement in accord with any of the numerous well known techniques for determining porosity.

The first step of the inventive method is to perform nonwetting fluid intrusion measurements on a porous sample to generate capillary pressure data indicative of the volume of intruded fluid versus the applied pressure. This step may be performed in accord with any of a variety of known procedures. Above-mentioned U.S. Pat. No. 4,211,106 discloses one such data-gathering procedure in which mercury is used as the nonwetting fluid.

To perform nonwetting fluid intrusion measurements, a sample with substantially evacuated pore space is immersed in nonwetting fluid. Some of the fluid is forced into the pore space of the sample under quasi-static conditions as the fluid pressure is increased by increments. For each externally applied pressure, the decrease in the volume of fluid surrounding the sample is measured. Because a porous sample will normally repulse a nonwetting fluid from its surfaces, so that pressure is required to force nonwetting fluid into the pores of the sample, the volume of fluid intruded into the pores of the sample is determined at each externally applied pressure. A variety of porosimeter systems for performing nonwetting fluid intrusion measurements are commercially available. An example is the Auto Pore 9200, manufactured by Micromeritics Instrument Corporation, 5680 Joshen Springs Rd., Norcross, Georgia 30093.

Once the capillary pressure data are measured, the data preferably are displayed as a graph such as FIG. 1. FIG. 1 shows a typical mercury intrusion curve where the volume of intruded mercury (normalized by the total pore volume) is plotted versus the applied pressure. The FIG. 1 data were generated from measurements on a sample of quartz cemented sandstone grains. For each externally applied pressure (plotted on the lower horizontal scale of FIG. 1), the local diameter of the interface between the pore space and the nonwetting fluid (mercury) is determined by the capillary pressure equation:

$$p = -4\gamma(\cos\theta)/l$$

where p is the capillary pressure (i.e. the difference in pressures on the two sides of the meniscus), $\gamma$ is the surface tension (for mercury, this is equal to 485 dyn/cm), $\theta$ is the contact angle (for mercury, this is usually taken to be 130°), and l is the local diameter of the pore space. The capillary pressure equation assumes a cylindrical local geometry. The upper horizontal scale of FIG. 1 shows pore diameter, l, as computed from the capillary pressure using the capillary pressure equation.

With reference to FIG. 1, the initial portion of the intrusion curve with positive curvature is associated with surface defects and intrusion into the corners of sample edges. In accord with the inventive method, the inflection point of the rapidly rising portion of the curve is taken to mark the threshold pressure $p_c$ associated with formation of the first connected path spanning the sample. From the capillary pressure equation, we conclude that the pore widths l included in the infinite cluster satisfy the relation $l > -4\gamma(\cos\theta)/p_c$; moreover, it is not possible to form a connected cluster such that the included pore widths are strictly greater than $-4\gamma(\cos\theta)/p_c$.

Thus, the characteristic length, $l_c$, in equation (1), (2), and (3) is determined to be $l_c = (-4)\gamma\cos\theta/(p_c)$.

A preferred embodiment permits determination of the sample's electrical conductivity and permeability from the measured capillary pressure data by extracting therefrom the parameters $l_{max}^\sigma$, $S_{max}^\sigma$, $l_{max}^k$, and $S_{max}^k$ which appear in equations (1) and (2). These parameters may be extracted graphically by producing new graphs of the measured data.

These new graphs may be generated as follows. First, one subtracts the intruded volume associated with the threshold pressure $p_c$ from all volume coordinates of the measured data points, thus producing a set of modified data points. This subtraction is equivalent to setting the ordinate of the FIG. 1 injection curve equal to zero at $p = p_c$ (or at $l = l_c$). The subtraction step is performed because the small volume of fluid that intrudes into the sample at pressures below $p_c$ intrudes mostly into defects along the sample surface and into pores not connected to the first connected cluster.

Figure 2:
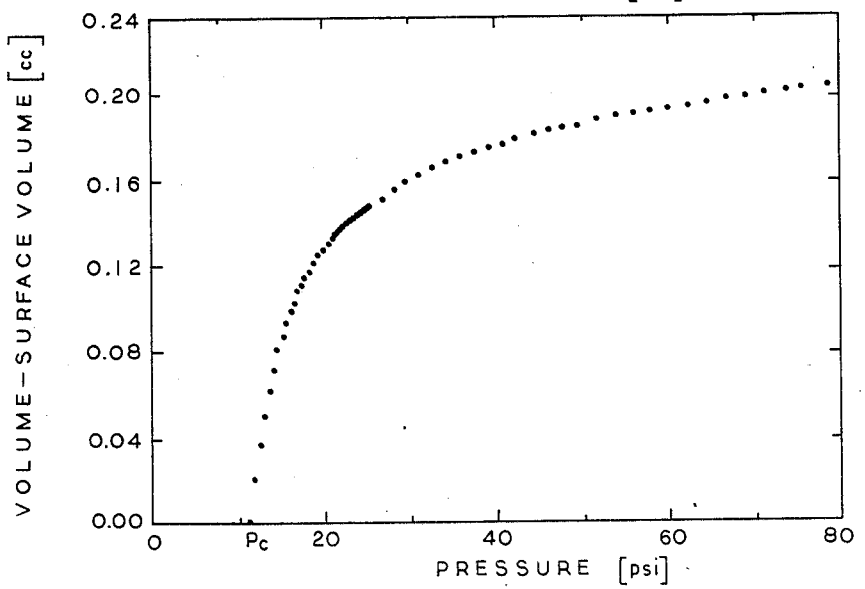
FIG. 2 is a mercury intrusion curve that has been modified by subtracting from the ordinate the mercury volume (denoted as the "surface volume") that intrudes into the sample at pressure lower than the threshold pressure $p_c$. The horizontal axis is the external applied pressure. The vertical axis represents volume of intruded mercury minus surface volume (in cubic centimeters).

FIG. 2 is an example of a typical graph of capillary pressure data modified as described in the previous paragraph. The threshold pressure $p_c$ corresponds to the point at which the ordinate is equal to zero.

The volume fraction of pore space filled with nonwetting fluid as a function of capillary pressure or pore diameter l corresponds to the saturation function S(l). Thus, the modified data points graphed in FIG. 2 determine the function S(l). This follows from the fact that the nonwetting fluid traces out the "percolation" path (the path of least resistance) within the pore space. The position of the nonwetting fluid meniscus is controlled by the local capillary pressure. At a given pressure, p, the only pores accessible to the nonwetting fluid are those with pore diameters $l > |4\gamma(\cos\theta)/p|$ and which are reachable along paths that contain no pore diameters smaller than $|4\gamma(\cos\theta)/p|$. This set of accessible pores at a given pressure p is the same as the set of pores counted by the function S(l), which is defined as the set of connected pores with pore diameters of size l and larger.

Figure 3:
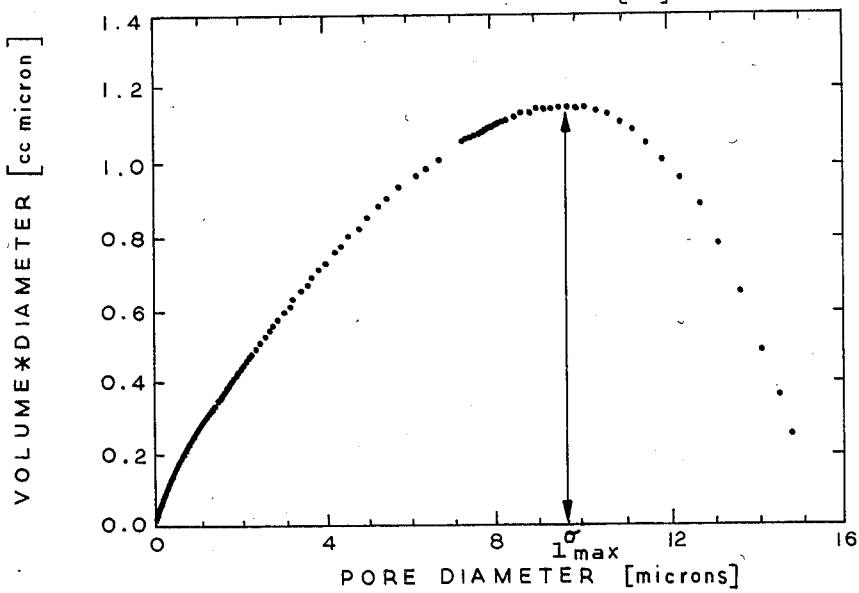
FIG. 3 is a graph of the FIG. 2 data where the ordinate of each data point has been multiplied by the parameter l, where each value of l is the pore diameter related to a particular value of applied pressure, p, by the capillary pressure equation set out in the specification. Distance away from the vertical axis represents the parameter l. The point on the FIG. 3 curve which has maximum ordinate corresponds to the pore diameter $l_{max}^\sigma$.
Figure 4:
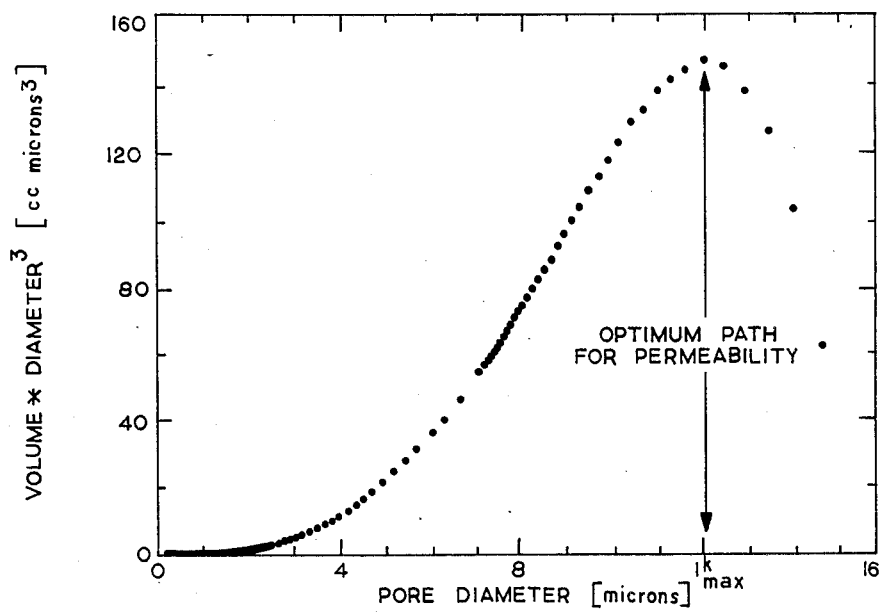
FIG. 4 is a graph of the FIG. 2 data, where the ordinate of each data point has been multiplied by the parameter $(l)^3$. Distance away from the vertical axis represents the parameter l. The point on the FIG. 4 curve which has maximum ordinate corresponds to the pore diameter $l_{max}^k$.

In a preferred embodiment, the ordinate of each modified data point of FIG. 2 is multiplied by a factor of l and plotted versus the parameter l to produce the graph of FIG. 3. Also in this embodiment, the ordinate of each modified data point of FIG. 2 is multiplied by a factor of $l^3$ and plotted versus the parameter l to produce the graph of FIG. 4. Each of the values of the parameter l which comprise the horizontal scale of FIGS. 3 and 4, is related to an external applied pressure, p, by the capillary pressure equation $p = -4\gamma(\cos\theta)/l$.

The maximum of the FIG. 2 curve determines $l_{max}^\sigma$ as well as the corresponding value of $S_{max}^\sigma$. $S_{max}^\sigma$ is simply the ordinate of the point on FIG. 2 corresponding to the pressure in turn corresponding to $l_{max}^\sigma$. The maximum of the FIG. 3 curve determines $l_{max}^k$ as well as the corresponding value of $S_{max}^k$. $S_{max}^k$ is similarly the ordinate of the point of FIG. 2 corresponding to the pressure corresponding in turn to $l_{max}^k$.

Figure 5:
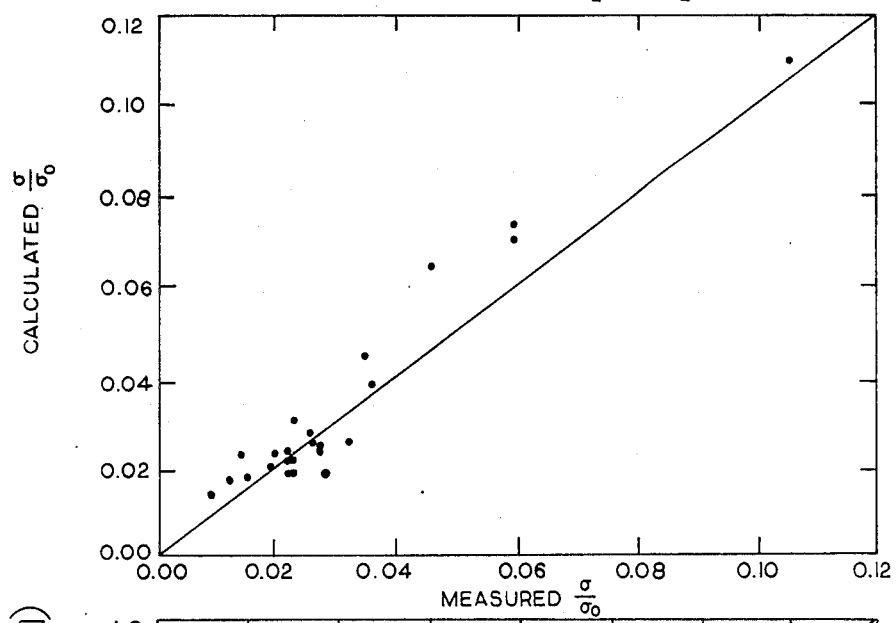
FIG. 5 is a graph of values of the conductivity formation factor $\sigma/\sigma_0$ for a group of sandstone samples calculated in accordance with the invention from capillary pressure data obtained from mercury intrusion measurements on the samples, versus independently measured values of the conductivity formation factor. Each point on FIG. 5 corresponds to both a set of mercury intrusion measurements, and an independent conductivity measurement on the same sample.
Figure 6:
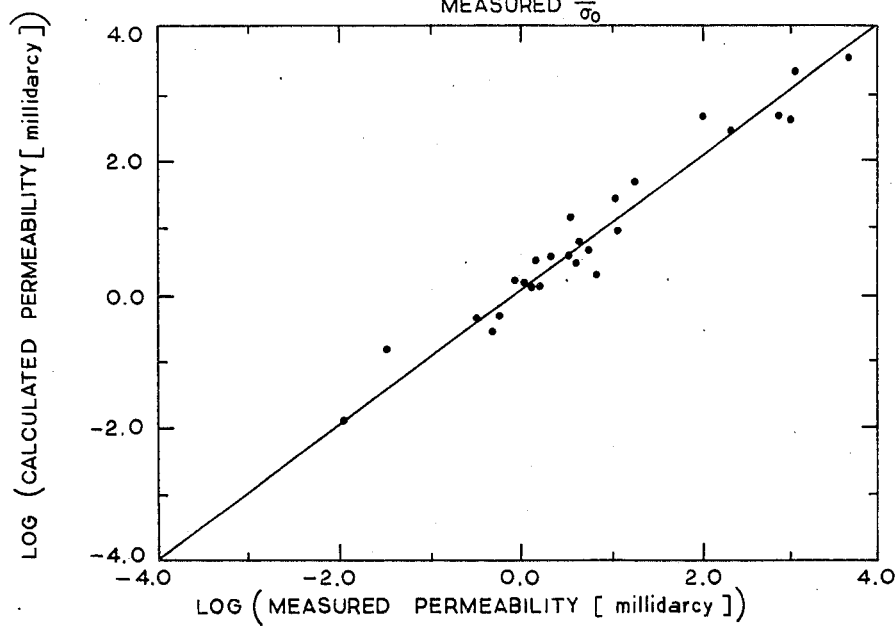
FIG. 6 is a graph of values of absolute permeability calculated in accordance with the invention from the same mercury intrusion data as were used to generate FIG. 5, versus independently measured values of the absolute permeability. Each point of the FIG. 6 curve corresponds to both a set of mercury intrusion measurements, and an independent permeability measurement on the same sample.

We have calculated the conductivity and permeability of each of a number of sandstone samples (ranging in porosity from 6% to 35%) using capillary pressure data obtained from mercury intrusion measurements on each such sample. FIG. 5 shows the calculated conductivity ratio (or "formation factor") $\sigma/\sigma_0$ (plotted on the vertical axis) from equation (1) versus an independently measured value of the ratio $\sigma/\sigma_0$ (plotted on the horizontal axis) for each sample. FIG. 6 shows the calculated permeability (plotted on the vertical axis) from equation (2), versus an independently measured absolute permeability (plotted on the horizontal axis) for each sample.

Figure 7:
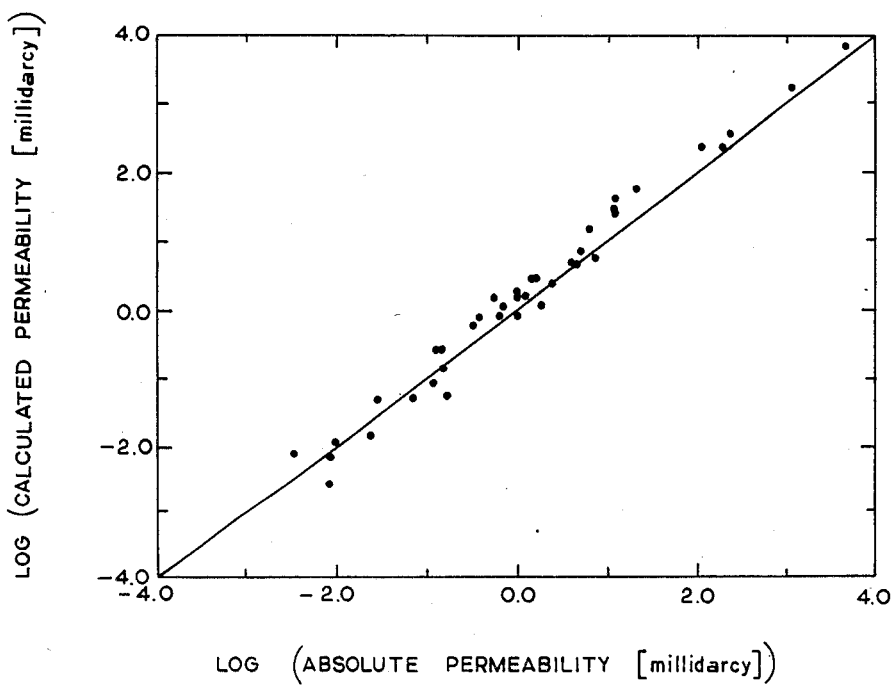
FIG. 7 is a graph of absolute permeabilities calculated in accord with an alternative embodiment of the invention from mercury intrusion data (from the same samples characterized by FIGS. 5 and 6), versus independently measured values of the absolute permeability. Each point of the FIG. 7 curve corresponds to both a set of mercury intrusion measurements, and an independent permeability measurement, on the same sample.

In an alternative embodiment in which the conductivity ratio $\sigma/\sigma_0$ for a sample is independently known, only parameter $l_c$ need be extracted from capillary pressure data obtained from nonwetting fluid intrusion measurements performed on the sample in the manner described above. Then, the permeability of the sample is determined from equation (3) and the known conductivity ratio. FIG. 7 shows the calculated permeability (plotted on the vertical axis) from equation (3), versus the independently measured absolute permeability (plotted on the horizontal axis) for each of a set of samples.

Figure 8:
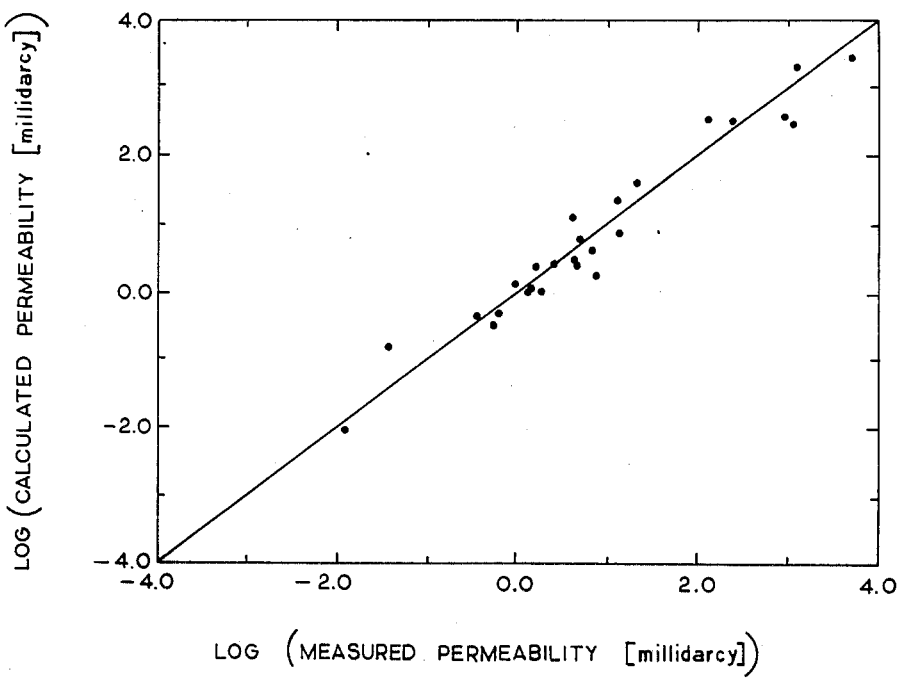
FIG. 8 is a graph of absolute permeabilities calculated in accord with an alternative embodiment of the invention from mercury intrusion data (from the same samples characterized by FIGS. 5 and 6), versus independently measured values of the absolute permeability. Each point of the FIG. 8 curve corresponds to both a set of mercury intrusion measurements, and an independent permeability measurement, on the same sample.

In yet another variation on the inventive method, the parameters $l_c$, $l_{max}^\sigma$ and $S_{max}^\sigma$ are extracted from capillary pressure data for a sample, and the permeability of the sample is determined from equation (3) using the conductivity ratio (or "formation factor") $\sigma/\sigma_0$ calculated from equation (1). FIG. 8 shows permeabilities (for the same set of samples characterized by FIGS. 5 and 6) calculated in accord with the variation described in the preceding sentence, versus independently measured absolute permeabilities (plotted on the horizontal axis) for the samples.

It is emphasized that the mercury injection curves, absolute permeabilities, and conductivities associated with each point plotted on FIGS. 5, 6, 7, and 8 were measured on the same piece of rock sample. It is also emphasized that the calculated values do not involve adjustable parameters. The agreement between measured and calculated values is within experimental error.

Although the foregoing embodiments have been described with reference to displayed graphs of the measured data (or modified versions of the measured data) it is within the scope of the invention to extract the desired parameters from the measured data by processing the data in a suitable computer. To accomplish this, the above-described procedures are translated into a series of computer instructions in a manner that will be apparent to those ordinarily skilled in the art of computer programming. In one variation on this embodiment, the measured capillary pressure data are digitized and the digitized signals are processed in a computer. In this class of embodiments, no display of the measured data, or of the measured data after intermediate processing steps have been performed thereon, need be produced.

The above description is merely illustrative of the invention. Various changes in the details of the methods described may be within the scope of the appended claims without departing from the spirit of the invention.

We claim:

1. A method for determining pore-dependent properties of a porous sample, including the steps of:
   (a) performing nonwetting fluid intrusion measurements on the sample to generate capillary pressure data indicative of the volume of intruded fluid versus applied pressure; and
   (b) determining from the capillary pressure data the threshold capillary pressure, $p_c$, by organizing the data as a graph of intruded fluid volume versus pore diameter and identifying $p_c$ as the inflection point of the rapidly rising portion of the graph, from which the associated characteristic length, $l_c$, may be determined to be $l_c = (-4)\gamma(\cos \theta)/(p_c)$, where $\gamma$ is the surface tension of the nonwetting fluid and $\theta$ is the contact angle.

2. The method of claim 1, also including the step of:
   (c) determining from the capillary pressure data the the pore diameter, $l_{max}^\sigma$, at which the product of intruded fluid volume and pore diameter is a maximum, and the parameter $S_{max}^\sigma$ equal to the fraction of pore space filled at $l_{max}^\sigma$.

3. The method of claim 2, also including the step of displaying the capillary pressure data as a graph of the product of intruded fluid volume and pore diameter, versus pore diameter.

4. The method of claim 1, also including the step of:
   (d) determining from the capillary pressure data the parameter $l_{max}^k$ equal to the pore diameter at which the product of the cube of pore diameter and intruded fluid volume is a maximum, and the parameter $S_{max}^k$ equal to the fraction of pore space filled at $l_{max}^k$.

5. The method of claim 4, also including the step of displaying the capillary pressure data as a graph of the intruded fluid volume multiplied by the cube of the pore diameter, versus pore diameter.

6. The method of claim 4, also including the step of:
   (e) determining the absolute permeability, k, of the sample from the relation $k = 1/84 (l_{max}^k/l_c)(l_{max}^k)^2 \cdot S_{max}^k \cdot \Phi$, where $\Phi$ is the porosity of the sample.

7. The method of claim 1, also including the step of displaying the capillary pressure data as a graph of intruded fluid volume versus pore diameter.

8. The method of claim 7, also including the step of displaying the capillary pressure data as a graph of the product of intruded fluid volume and pore diameter, versus pore diameter.

9. The method of claim 7, also including the step of displaying the capillary pressure data as a graph of the intruded fluid volume multiplied by the cube of the pore diameter, versus pore diameter.

10. The method of claim 1, also including the step of
    (f) determining the absolute permeability, k, of the sample from the relation $k = (1/217)(l_c)^2 \sigma/\sigma_0$, where $\sigma/\sigma_0$ is the known product of the electrical conductivity, $\sigma$, of the sample when saturated with a liquid and the quantity $(\sigma_o)^{-1}$ where $\sigma_o$ is the electrical conductivity of the liquid.

11. The method of claim 1, wherein the nonwetting fluid is mercury.

12. A method for determining pore-dependent properties of a porous sample, including the steps of:
    (a) performing nonwetting fluid intrusion measurements on the sample to generate capillary pressure data indicative of volume of intruded fluid versus applied pressure;
    (b) determining from the capillary pressure data the threshold capillary pressure, $p_c$, and the associated characteristic length, $l_c=(-4)\gamma(\cos\theta)/p_c$, where $\gamma$ is the nonwetting fluid surface tension and $\theta$ is the contact angle; and (c) determining, from the capillary pressure data, the pore diameter, $l_{max}{}^\sigma$, at which the product of capillary diameter and the intruded fluid volume is a maximum, and the fraction $S_{max}{}^\sigma$, of connected pore space filled with nonwetting fluid at the applied pressure corresponding to $l_{max}{}^\sigma$;

(d) determining the ratio, $\sigma/\sigma_0$, from the expression $\sigma/\sigma_0=(l^\sigma max/l_c)(\Phi)(S_{max}{}^\sigma)$, where $\Phi$ is the porosity of the sample, $\sigma$ is the electrical conductivity of the sample when saturated with liquid, and $\sigma_o$ is the electrical conductivity of the liquid.

13. The method of claim 12, also including the step of:

(e) determining the absolute permeability, k, of the sample from the relation $$k=(1/217)(l_c)^2(\sigma/\sigma_0).$$

14. The method of claim 12, wherein the nonwetting fluid is mercury.

15. The method of claim 12, including the step of displaying the measured capillary pressure data as a capillary pressure curve, and identifying $p_c$ as the inflection point of the rapidly rising portion of the curve.

16. A method for determining pore-dependent properties of a porous sample, including the steps of:

(a) performing mercury intrusion measurements on the sample to generate capillary pressure data indicative of volume of intruded mercury versus applied pressure;

(b) determining from the capillary pressure data the threshold capillary pressure, $p_c$, and the associated characteristic length $l_c=(-4)\gamma(\cos\theta)/p_c$, where $\gamma$ is the surface tension of mercury and $\theta$ is the contact angle;

(c) determining from the capillary pressure data the parameter $l_{max}{}^k$, where $l_{max}{}^k$ is equal to the pore diameter at which the product of the cube of pore diameter and the volume of intruded mercury is a maximum, and the parameter $S_{max}{}^k$, where $S_{max}{}^k$ is the fraction of connected pore space filled with mercury at the applied pressure corresponding to $l_{max}{}^k$; and (d) determining from the capillary pressure data the parameter $l_{max}{}^\sigma$, where $l_{max}{}^\sigma$ is equal to the pore diameter at which the product of pore diameter and the volume of intruded mercury is a maximum, and the parameter $S_{max}{}^\sigma$, where $S_{max}{}^\sigma$ is the fraction of connected pore space filled with mercury at the applied pressure corresponding to $l_{max}{}^\sigma$.

17. The method of claim 16, wherein the permeability, k, of the sample is identified as $k=1/84\,(l_{max}{}^k/l_c)(l_{max}{}^k)^2 S_{max}{}^k\Phi$, and the electrical conductivity, $\sigma$, of the sample when saturated with a liquid is identified as $\sigma=(\sigma_o)(l_{max}{}^\sigma/l_c)(S_{max}{}^\sigma)\Phi$, where $\Phi$ is the sample porosity, and $\sigma_o$ is the electrical conductivity of the liquid.

* * * * *